US010233509B2

(12) United States Patent
Wong et al.

(10) Patent No.: US 10,233,509 B2
(45) Date of Patent: Mar. 19, 2019

(54) METHOD FOR DETECTION CPV 2A, 2B, AND 2C AND FOR DISCRIMINATION WILD TYPE FROM VACCINE TYPE

(71) Applicant: Credo Biomedical Pte Ltd., Singapore (SG)

(72) Inventors: Jr Winston Wong, New Taipei (TW); Stephen Chang-Chi Kao, New Taipei (TW); Ying-Ta Lai, New Taipei (TW); Ming-Lung Hung, New Taipei (TW); Wei-Chen Wang, New Taipei (TW)

(73) Assignee: Credo Biomedical Pte Ltd., Singapore (SG)

( * ) Notice: Subject to any disclaimer, the term of this patent is extended or adjusted under 35 U.S.C. 154(b) by 0 days.

(21) Appl. No.: 15/371,223

(22) Filed: Dec. 7, 2016

(65) Prior Publication Data

US 2018/0155797 A1 Jun. 7, 2018

(51) Int. Cl.
*A61K 39/395* (2006.01)
*C07H 21/04* (2006.01)
*C12N 15/00* (2006.01)
*C07H 21/02* (2006.01)
*A61K 39/00* (2006.01)
*C12Q 1/70* (2006.01)
*C12Q 1/6823* (2018.01)

(52) U.S. Cl.
CPC ............ *C12Q 1/701* (2013.01); *C12Q 1/6823* (2013.01); *C12Q 2600/112* (2013.01); *C12Q 2600/156* (2013.01); *C12Q 2600/158* (2013.01)

(58) Field of Classification Search
CPC .... C07K 14/47; C07K 16/30; C07K 2317/34; A61K 2039/505; A61K 39/00
See application file for complete search history.

(56) References Cited

U.S. PATENT DOCUMENTS

2007/0042354 A1   2/2007   Engelhard

FOREIGN PATENT DOCUMENTS

| AU | 2008266120 | 12/2008 |
|---|---|---|
| CN | 103757139 B | 5/2015 |
| CN | 105463132 A | 4/2016 |
| CN | 105803112 | 7/2016 |
| CN | 105838826 | 8/2016 |
| JP | 2010-530853 A | 9/2010 |
| JP | 2014-512811 A | 5/2014 |
| WO | 2012/128616 | 9/2012 |

OTHER PUBLICATIONS

Hingonekar Namrata Ramdas, Molecular Characterization of VP2 gene of canine parvo virus from vaccinal strains, Department of animal biotechnology college of veterinary science and animal husbandry anand agricultural university anand-388001 (Gujarat), 2011, XP055413936.
Vasileios Ntafis et al., Characterization of Canine parvovirus 2 variants circulating in Greece, Brief Research Reports, 2010, pp. 737-740, J Vet Diagn Invest 22, XP055413919.
Decaro et al., "Diagnostic tools based on minor groove binder probe technology for rapid identification of vaccinal and field strains of canine parvovirus type 2b." Journal of Virological Methods 138 (2006), p. 10-16, Epub Sep. 5, 2006.
Decaro et al., "Long-term viremia and fecal shedding in pups after modified-live canine parvovirus vaccination" Vaccine 32 (2014) 3850-3853, Apr. 30, 2014.
Decaro et al., "A minor groove binder probe real-time PCR assay for discrimination between type 2-based vaccines and field strains of canine parvovirus", Journal of Virological Methods, 136 (2006), p. 65-70, May 6, 2006.
Nicola Decaro et al., A real-time PCR assay for rapid detection and quantitation of canine parvovirus type 2 in the feces of dogs, Veterinary Microbiology 105 (2005) 19-28, Apr. 14, 2004, pp. 19-28, XP027620340, Elsevier.
Lijun Shi et al., Full Length Research Paper, Establishment and evaluation of a novel TaqMan probe-based real-time PCR for detection of Canine Parvovirus, African Journal of Microbiology Research vol. 6(13), pp. 3134-3138, Apr. 9, 2012, XP055393426.
T. Hirasawa et al., Differentiation of Wild- and Vaccine-type Canine Parvoviruses by PCR and Restriction-enzyme Analysis, J. Vet. Med. B 42, 601-610 (1995), Apr. 18, 1995, XP055393226, 1995 Blackwell Wissenschafts—Verlag, Berlin.
Gali Bingga et al., High resolution melting curve analysis as a new tool for rapid identification of canine parvovirus type 2 strains, Molecular and Cellular Probes, Aug. 8, 2014, pp. 271-278, XP055393447, Elsevier.
Marina Gallo et al., Evolution of Canine Parvovirus in Argentina between years 2003 and 2010: CPV2c has become the predominant variant affecting the domestic dog population, Virus Research, Dec. 17, 2010, pp. 106-110, XP028372426, Elsevier.
N. Decaro et al., New Approaches for the Molecular Characterization of Canine Parvovirus Type 2 Strains, J. Vet. Med. B 52, © 2005 Blackwell Verlag, Berlin, Jul. 15, 2005, pp. 316-319.
Carla Miranda et al., "Canine parvovirus: the worldwide occurrence of antigenic variants", Journal of General Virology (2016), 97, pp. 2043-2057 © 2016 The Authors, Printed in Great Britain, Sep. 2016.

*Primary Examiner* — Barry A Chestnut
(74) *Attorney, Agent, or Firm* — Winston Hsu

(57) ABSTRACT

The present invention disclose a method for detection CPV 2a, 2b, and 2c in a sample by detecting VP2 gene. The signals can be detected by both fluorescent detection system and lateral flow immunochromatographic assay. The second object of this present invention is to provide a method to discriminate the wild type from the vaccine type. The first approach to achieve this object is discriminating wild type from vaccine type by SNP 36, which could be used on both fluorescent detection system and lateral flow immunochromatographic assay. The second approach to achieve this object is discriminating wild type from vaccine type by SNP 899 and SNP 963.

7 Claims, 6 Drawing Sheets

Specification includes a Sequence Listing.

METHOD FOR DETECTION CPV 2A, 2B, AND 2C AND FOR DISCRIMINATION WILD TYPE FROM VACCINE TYPE

BACKGROUND OF THE INVENTION

1. Field of the Invention

This invention is related to a CPV 2a, 2b, 2c detection method in dog sample. More particular, this invention is related to distinguish vaccine type from wild type.

2. Description of the Prior Art

The canine parvovirus type 2 (hereinafter CPV-2) infection is a highly contagious viral illness that affects dogs, and from dogs to dogs, characterized by severe leucopenia, vomiting, weight loss, lack of appetite (anorexia) and hemorrhagic diarrhea. Infection is acquired through direct oral or nasal contact with virus-containing feces or indirectly through contact with virus-contaminated fomites. As often happens, dogs acquire CPV through natural infection, and the majority of CPV infected cases are seen in puppies that are between six weeks and six months old. The CPV-2 infections have been emerged to be a serious problem in dogs in recent times around the world due to the increase of the laboratory dogs and pet dogs.

The genome of CPV-2 is a single stranded negative sense DNA with size of 5.2 Kb in length which has two promoters resulting in the expression of three structural (VP1, VP2 and VP3), and two non-structural proteins (NS1 and NS2) through alternate splicing of the viral mRNAs. VP2 (64 kDa) is an $NH_2$-terminally truncated form of VP1 (84 kDa) and is the major component of the capsid (90%) which is a key factor of the antigenicity. CPV-2 emerged in the late 1970s, but it was replaced in a few years by its antigenic variants. Currently, three main antigenic variants of CPV-2 are known as type 2a, 2b, and 2c (hereinafter CPV-2a, CPV-2b, and CPV-2c) and variously distributed in dog population worldwide. The original type 2 is still present in the CPV-2 vaccine available on the market although disappeared from the field.

Virus is shed in the feces of infected dogs within 4-5 days after infection which is often before clinical signs occurs. The virus shedding can be detected throughout the period of illness, until about 10 days after clinical recovery. Therefore, feces samples are commonly used in diagnostic tests. The diagnostic tests includes HA (Haemagglutination), Electron Microscopy (EM), virus isolation using in MDCK, CRFK or A72 cell line, Enzyme Linked Immunosorbent Assay (ELISA), Latex Agglutination Test (LAT), Fluorescent Antibody Test (FAT), CIE test, Virus neutralization test, PCR, real time PCR, loop-mediated isothermal amplification (LAMP), nucleic acid hybridization, in situ hybridization, and nucleic acid sequencing, each of them is with varying degree of sensitivity and specificity and will sometimes yield false positive cases. Among the above-mentioned diagnostic tests, PCR and real time PCR are most commonly used and with relatively higher accuracy and specificity methods for CPV-2a, CPV-2b, and CPV-2c diagnosis.

The incidence of CPV-2a, CPV-2b, and CPV-2c infections has been reduced radically by early vaccination in young puppies. Some popular vaccines are Duramune MX5, Canivac 5, Vanguarad plus 5 L4 CV, Nobivac Puppy DP, Canine 6II-SL, Eurican5, Virbagen DA2Parvo. However, diagnosis of CPV-2a, CPV-2b, and CPV-2c may be ambiguous when carried out on fecal samples from dogs presenting with diarrhea few days after vaccination. In fact, the modified-live virus contained in the vaccines is able to replicate in the intestinal mucosa of vaccinated dogs, despite the unnatural route of administration, and to be shed in the feces albeit at low titers and for a shorter time period with respect to the wild strands. In such a circumstance, the detection of the nucleic acid of CPV-2a, 2b, and 2c in the feces of vaccinated dogs could be false-positive, leading to a misdiagnosis of the infection.

Due the above-mentioned circumstance, it is necessary to develop an assay with high accuracy and stability for detecting CPV-2a, CPV-2b, and CPV-2c, and for discriminating wild type from vaccine type.

SUMMARY OF THE INVENTION

The object of this present invention is to provide detection method of the target nucleic acid of the VP2 gene of CPV 2a, 2b, and 2c which overcomes the disadvantages of the prior art as described above. The object of the present invention is in particular to provide methods for the detection of the target nucleic acid in which the target nucleic acid is amplified with a designated probe, a pair of primers which are specific to the target nucleic acid, and a template-dependent polymerase with ability of exonuclease hydrolysis. This object is achieved according to the invention by a method for the detection of a target nucleic acid in a suspected sample comprising the following steps:

(a) To provide a sample suspected to contain the target nucleic acid of VP2 of CPV type 2a, 2b, and 2c.

(b) To provide a pair of primers comprising a forward and a reverse primer which the forward primer consists of at least contiguous 12 nucleotides of a nucleic acid sequence selected from the nucleic acid sequence SEQ ID: 2 of VP2 gene, and the reverse primer consists of at least contiguous 12 nucleotides selected from the complementary nucleic acid sequence SEQ ID NO: 3.

(c) To amplify the target nucleic acid with a template-dependent polymerase.

(d) To anneal the probe to the target nucleic acid to form a hybridized product during step (c) wherein the probe sequence is selected from a group comprising SEQ ID NO:4 to 6, and (e) To detect signals generating from the hybridized product as an indicator of the presence of the target nucleic acid of the CPV type 2a, 2b, and 2c.

According to the present invention, the signals generating from the hybridized product can be detected by both fluorescent detection system and lateral flow immunochromatographic assay. If the signals are detected by either fluorescent detection system or lateral flow immunochromatographic assay, the presence of the signals is indicative of the presence of the CPV 2a, 2b, and 2c in the suspected sample, and the absence of the signals is indicative of the absence of the CPV 2a, 2b, and 2c in the suspected sample.

The second object of this present invention is to provide two methods to discriminate the wild type from the vaccine type. The first method to achieve this object is discriminating wild type from vaccine type by SNP 36. The target nucleic acid is amplified with above-mentioned probe, a pair of primers which are specific to the target nucleic acid, and a template-dependent polymerase with ability of exonuclease hydrolysis. This object is achieved according to the invention by a method for the detection of a target nucleic acid comprising the following steps:

(a) To provide a sample suspected to contain the target nucleic acid of VP2 of CPV type 2a, 2b, and 2c.

(b) To provide a pair of primers comprising a forward and a reverse primer which the forward primer consists of at least contiguous 12 nucleotides of a nucleic acid sequence selected from the nucleic acid sequence SEQ ID: 7 of VP2 gene, and the reverse primer consists of at least contiguous 12 nucleotides selected from the complementary nucleic acid sequences SEQ ID NO: 11, 12, or 13.

(c) To amplify the target nucleic acid with a template-dependent polymerase.

(d) To anneal the probe to the target nucleic acid to form a hybridized product during step (c) wherein the probe sequence is selected from a group comprising SEQ ID NO:14 and 15, and (e) To detect signals generating from the hybridized product as an indicator of the presence of the target nucleic acid.

The signals generating from the hybridized product can be detected by both fluorescent detection system and lateral flow immunochromatographic assay. If the signals are detected by either fluorescent detection system or lateral flow immunochromatographic assay, the presence of signals is indicative of the wild type, and the absence of fluorescent signal is indicative of the vaccine type.

The second method to achieve this object is discriminating wild type from vaccine type by SNP 899 and SNP 963. The amplification conditions and detection steps are identical to the SNP36, except below conditions:

a) Forward primer: consists of at least contiguous 12 nucleotides of a nucleic acid sequence selected from the nucleic acid sequence SEQ ID: 16 of VP2 gene b) Reverse primer: consists of at least contiguous 12 nucleotides selected from the complementary nucleic acid sequences SEQ ID NO: 22 or 23, c) Probes: the first probe is specific to SNP 899 of the VP2 gene, and the second probe is specific to SNP 963 of the VP2 gene. The first probe is selected from a group consisting of SEQ ID NO: 24 to 28, and the second is selected from a group consisting of SEQ ID NO: 29 to 33.

The signals generating from the hybridized product can be detected by fluorescent detection system. The presence of both distinct signals is indicative of the vaccine type, and the presence of any one of the distinct fluorescent signals is indicative of the vaccine type.

This SUMMARY is provided to briefly identify some aspects of the present invention that are further described below in the DETAILED DESCRIPTION. This SUMMARY is not intended to identify key or essential features of the present disclosure nor is it intended to limit the scope of any claims.

The term "aspects" is to be read as "at least one aspect." The aspects described above and other aspects of the present disclosure described herein are illustrated by way of example(s) and not limited in the accompanying drawing.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
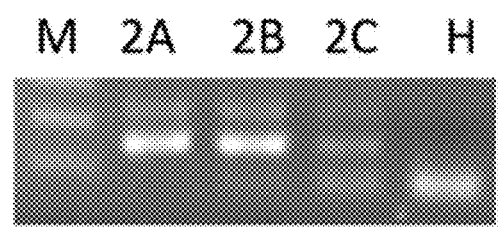
FIG. 1 illustrates the amplification products derived from the embodiment 1 by means of agarose gel electrophoresis.

The following merely illustrates the principles of the invention. It will thus be appreciated that those skilled in the art will be able to devise various arrangements which, although not explicitly described or shown herein, embody the principles of the invention and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements later developed that perform the same function, regardless of structure.

Unless otherwise explicitly specified herein, the drawings are not drawn to scale.

In order to solve the questions mentioned above, the present invention provides a PCR or real-time PCR assay for rapid identification of CPV 2a, 2b, and 2c using TaqMan probes with conjugated minor groove binder (MGB) ligands.

In such assays, labeling the type-specific probes with different fluorescent reporter has ensured the detection of type-specific fluorescence. The Taq polymerase applied in this assay is a DNA-dependent polymerase with nexonuclease hydrolysis function. The fluorescent signals are detected by the quantity of the fragment of the fluorescent reporter which are cleaved from the probe hybridized to the target nucleic acid by an exonuclease hydrolysis of the DNA-dependent polymerase. The primer and/or probe comprise(s) a modified nucleotide or a non-nucleotide compound.

In one embodiment of the present invention, a method is provided for the detection of a target nucleic acid comprising the nucleic acid sequence of CPV 2a, 2b, and 2c in a sample comprising the step of:
(a) To provide a sample suspected to contain the target nucleic acid of VP2 of CPV type 2a, 2b, and 2c.
(b) To provide a pair of primers comprising a forward and a reverse primer which the forward primer consists of at least contiguous 12 nucleotides selected from the nucleic acid sequence SEQ ID: 2 of VP2 gene, and the reverse primer consists of at least contiguous 12 nucleotides selected from the complementary nucleic acid sequence SEQ ID NO: 3.
(c) To amplify the target nucleic acid with a template-dependent polymerase.
(d) To anneal the probe to the target nucleic acid to form a hybridized product during step (c) wherein the probe sequence is selected from a group comprising SEQ ID NO:4 to 6, and
(e) To detect signals generating from the hybridized product as an indicator of the presence of the target nucleic acid of the CPV type 2a, 2b, and 2c.

Due to VP2 (SEQ ID: 1) is the conserved region of CPV 2a, 2b, and 2c, all primers and probes disclosed in the present invention are selected from VP2 gene. To be more precisely, the forward primer for detection of CPV 2a, 2b, and 2c are consisted of at least contiguous 12 nucleotides of a nucleic acid sequence selected from the nucleic acid sequence SEQ ID: 2, which is part of the VP2 gene, and the reverse primer consists of at least contiguous 12 nucleotides selected from the complementary nucleic acid sequence SEQ ID NO: 3. The probe, which is one of the group of SEQ ID NO: 4 to 6, is also specific to VP2 gene. The presence of the fluorescence signal is indicative CPV 2a, 2b, or 2c in a sample.

The present invention also discloses a method for discriminating the wild type from the vaccine by detecting SNP 36, SNP 899 and SNP 963 of VP2 gene. Regarding to SNP 36, the nucleotide is G for wild type and A for vaccine type, where the vaccine type means the sample had once vaccinated with one of the vaccine group including Duramune MX5, Canivac 5, Vanguarad plus 5 L4 CV, Nobivac Puppy DP, Canine 6II-SL, Eurican5, Virbagen DA2Parvo. And for SNP 899, the nucleotide is G for wild type and Duramune MX5 and C for vaccine type, where the vaccine type means the sample had once vaccinated with one of the vaccine group including Canivac 5, Vanguarad plus 5 L4 CV, Nobivac Puppy DP, Canine 6II-SL, Eurican5, Virbagen DA2Parvo. Lastly, in regard to SNP 963, the nucleotide is T for wild type, Canivac 5, Vanguarad plus 5 L4 CV, Nobivac Puppy DP, Canine 6II-SL, Eurican5, Virbagen and DA2Parvo, and A for vaccine type, where the vaccine type means the sample had once vaccinated with Duramune MX5. The TICD50 of the CPV of above-mentioned vaccines are greater or equal to $10^5$ copy. Therefore, the primers and probes are designed specific for the wild type of the present invention.

TABLE 1

The nucleotide of wild type and vaccine type

| Sample | SNP 36 | SNP 899 | SNP 963 |
|---|---|---|---|
| Wild type | G | G | T |
| Duramune MX5 | A | G | A |

TABLE 1-continued

The nucleotide of wild type and vaccine type

| Sample | SNP 36 | SNP 899 | SNP 963 |
|---|---|---|---|
| Canivac 5 | A | C | T |
| Vanguarad plus 5 L4 CV | A | C | T |
| Nobivac Puppy DP | A | C | T |
| Canine 6II-SL | A | C | T |
| Eurican5 | A | C | T |
| Virbagen DA2Parvo | A | C | T |

In another embodiment of the present invention, a method is provided for the discrimination wild type from vaccine type by SNP 36 comprising the step of:
(a) providing a sample suspected to contain the target nucleic acid,
(b) providing a pair of primers comprising a forward and a reverse primer wherein the forward primer consists of at least contiguous 12 nucleotides nucleic selected from the nucleic acid sequence SEQ ID:7, and the reverse primer consists of at least contiguous 12 nucleotides selected from the complementary nucleic acid sequences SEQ ID NO:11, 12, or 13,
(c) amplifying the subject with a template-dependent polymerase,
(d) annealing a SNP probe to the target nucleic acid to form a hybridized product during step (c), the SNP probe is specific to SNP 36 of the VP2 gene, and the SNP 36 probe sequence is SEQ ID NO:14 or 15,
(e) detecting the signals generating from the hybridized product as an indicator of the presence of the target nucleic acid.

SNP 36 can be applied solely to discriminate the wild type from the vaccine type. The forward primer of SNP 36 is consisted of at least contiguous 12 nucleotides of a nucleic acid sequence selected from the nucleic acid sequence SEQ ID: 7, or is selected one from the group of SEQ ID: 8 to 10. The reverse primer is selected one from the group of SEQ ID: 11 to 13. The probe is selected one from the group of SEQ ID: 14 to 15. The probe also carries a fluorescent reporter which is selected from the group comprising FAM, HEX, VIC, CY5, or TET, and the 3'-terminal of the probe carries a quencher which is selected from a group comprising TMARA, MGB, or BHQ. The presence of the fluorescent signal is indicative of wild type, and the absence of the fluorescent signal is indicative of the vaccine type. The vaccine type means the dog had once vaccinated with one of the vaccine group including Duramune MX5, Canivac 5, Vanguarad plus 5 L4 CV, Nobivac Puppy DP, Canine 6II-SL, Eurican5, Virbagen DA2Parvo. The presence of the fluorescent signal is indicative the wild type, and the absence of fluorescent signal is indicative of the vaccine type.

In still another embodiment of the present invention, a method is provided for the discrimination wild type from vaccine type by the combination of SNP 899 and SNP 963 comprising the step of:
(f) providing a subject suspected to contain VP2,
(g) providing a pair of primers comprising a forward and a reverse primer wherein the forward primer consists of at least contiguous 12 nucleotides selected from the nucleic acid sequence SEQ ID:16, and wherein the reverse primer consists of at least contiguous 12 nucleotides selected from the complementary nucleic acid sequences SEQ ID NO: 22 or 23,
(h) amplifying the subject with a template-dependent polymerase, (i) annealing two probes to the target nucleic acid to form a hybridized product during step (c) that one of the two probe is specific to SNP 899 of the VP2 gene, and the other probe is specific to SNP 963 of the VP2 gene, one probe is selected from a group consisting of SEQ ID NO: 24 to 27, and the other is selected from a group consisting of SEQ ID NO:29 to 33, (j) detecting two distinct fluorescent signals generating from the hybridized product.

The forward primer is consisted of at least contiguous 12 nucleotides selected from the nucleic acid sequence SEQ ID: 16, or is selected one from the group of SEQ ID: 17 to 21. The reverse primer is selected one from the group of SEQ ID: 22 to 23. The 5'-terminal of two probes also carry distinct fluorescent reporters which are selected from the group comprising FAM, HEX, VIC, CY5, or TET, and the 3'-terminal of the probes carry a quencher which are selected from a group comprising TMARA, MGB, or BHQ.

The probe of SNP 899 is selected one from the group of SEQ ID: 24 to 28, and the probe of SNP 963 is selected one from the group of SEQ ID: 29 to 33. The presence of the both fluorescent signal is indicative of wild type, and the presence of any one of the fluorescent signal is indicative of the vaccine type. The vaccine type means the dog had once vaccinated with one of the vaccine group including Duramune MX5, Canivac 5, Vanguarad plus 5 L4 CV, Nobivac Puppy DP, Canine 6II-SL, Eurican5, Virbagen DA2Parvo. The presence of both distinct fluorescent signals is indicative of the wild type, and the presence of any one of the distinct fluorescent signals is indicative of the vaccine type. The absence of both fluorescent signals is indicative of non-infected or low viral load sample.

The present invention using TaqMan probes is more sensitive than traditional method, where the limit of detection (hereinafter LOD) of present invention could reach $10^1$ copy on both CPV 2a, 2b, 2c detection and wild type/vaccine type discrimination. Furthermore, the specificity of CPV 2a, 2b, 2c detection and wild type/vaccine type discrimination is relatively high because the discrimination window could reach $10^8$ copy. Therefore, the present invention is suitable for rapid and unambiguous detection of CPV 2a, 2b, and 2c and discrimination wild type from vaccine type.

The present invention also provides a lateral flow immunochromatographic assay for rapid identification of CPV 2a, 2b, and 2c. The test results can be observed visually by the colored particles. In such assays, labeling the type-specific probes with different antigen has ensured the detection of type-specific analyte. The primer and/or probe c5'-terminal of either the forward or reverse primer carries an antigen which is selected from a group comprising FITC, DIG, Biotin, Texas-red and Tamra, and the 3'-terminal of the probe carries a distinct antigen from either the first or second primer which is selected from the group comprising FITC, DIG, Biotin, Texas-red and Tamra. The colored particle is selected from a group of colloidal gold, latex, and carbon nanoparticles.

The sequences of both primers and probes, the detection steps, and the amplifying conditions are identical to the Taqman probe detection method of CPV 2a, 2b, and 2c detection except the amount of forward primer is less than reverse primer, and the PNA is added and participated the amplifying step.

After the amplifying step is done, the analyte is added on the stripe to initiate the immunochromatographic assay. The presence of analyte signals in the test-line is indicative of the presence of the CPV 2a, 2b, and 2c in a sample, and the absence of analyte signals in the test-line is indicative of the absence of CPV 2a, 2b, and 2c.

Moreover, the present invention also provides a lateral flow immunochromatographic assay for discrimination wild type from vaccine type. The sequences of both primers and probes, the detection steps, and the amplifying conditions are identical to the SNP 36 detection except the amount of forward primer is less than reverse primer, and the PNA is added and participated the amplifying step. After the amplifying step is done, the analyte is added on the stripe to initiate the immunochromatographic assay. The presence of analyte signals in the test-line is indicative of the presence of the wild type, and the absence of analyte signals in the test-line is indicative of the vaccine type.

The present invention using lateral flow immunochromatographic assay is sensitive than traditional method, where the detection limit of present invention could reach $10^1$ copy on both CPV 2a, 2b, 2c detection and wild type/vaccine type discrimination. Besides, the present invention is also specific because it can still detect the CPV 2a, 2b, 2c, or SNP 36 while the vaccine titer is relatively high ($10^3$ copy). Therefore, the present invention using lateral flow immunochromatographic assay is suitable for rapid and unambiguous detection of CPV 2a, 2b, and 2c and discrimination wild type from vaccine type.

Embodiment 1 CPV 2a, 2b, and 2c Detection by Taqman Probe

Preferably, the present invention does not comprise the step of sample preparation. After purification or isolation of the nucleic acids including the target nucleic acid from a suspected sample, the target nucleic acid may be detected with different conditions.

One CPV2a infected sample, one CPV2b infected sample, one CPV2c infected sample, and one healthy sample are used in embodiment 1. The DNA was isolated by using an AXYGEN® AxyPrep Body Fluid Viral DNA/RNA. Primers having SEQ ID NO: 34 and SEQ ID NO: 3 were used to amplify a VP2 2a, 2b, and 2c sequence. The primer and probe sequences are shown in Table 2. The probe can also be replaced to SEQ ID No: 5 or SEQ ID No: 6.

TABLE 2

Primer Sequence

Primers used in the examples

| Sequence ID | Function | Sequence 5'-3' |
|---|---|---|
| SEQ ID No: 34 | Forward primer of VP2 | CTACCACAACAGGAGAAACA CCTGAGAG |
| SEQ ID No: 3 | Reverse primer of VP2 | CCTCCAATTGGATCTGTTGGT AGCAATAC |
| SEQ ID No: 4 | probe | GATTCAAAATATTAAC |

The amplification reaction is carried out which was measured and monitored in real-time on a BioRad CFX Connect Real-time System (BioRad Laboratories, Inc.). Each reaction mixture volume was 20 µl, and was amplified under the following conditions:

TABLE 3

Conditions of the Amplification of the reference samples

|  | 2a | 2b | 2c | Healthy |
|---|---|---|---|---|
| DNA template |  | 1 μl |  |  |
| Primer (F) |  | 0.5 μM |  |  |
| Primer (R) |  | 0.5 μM |  |  |
| Probe |  | 0.2 μM |  |  |
| dNTP |  | 0.25 mM |  |  |
| Polymerase |  | 5 unit |  |  |
| Total Volume |  | 20 μl |  |  |

The reaction mixtures were firstly incubated for 1 minutes at 95° C. The actual amplification reaction was carried out for 50 cycles according to the following scheme:

95° C. 1 sec.→65° C. 1 sec.

FIG. 1 shows the PCR products of the corresponding region, that is VP2, by means of agarose gel. The "H" represents healthy sample, and the "M" represents marker. It demonstrates that the PCR reactions with the given primer do exhibit none or less cross reactivity or amplification of unspecific sequences on both wild type samples and vaccine type samples.

Figure 2:
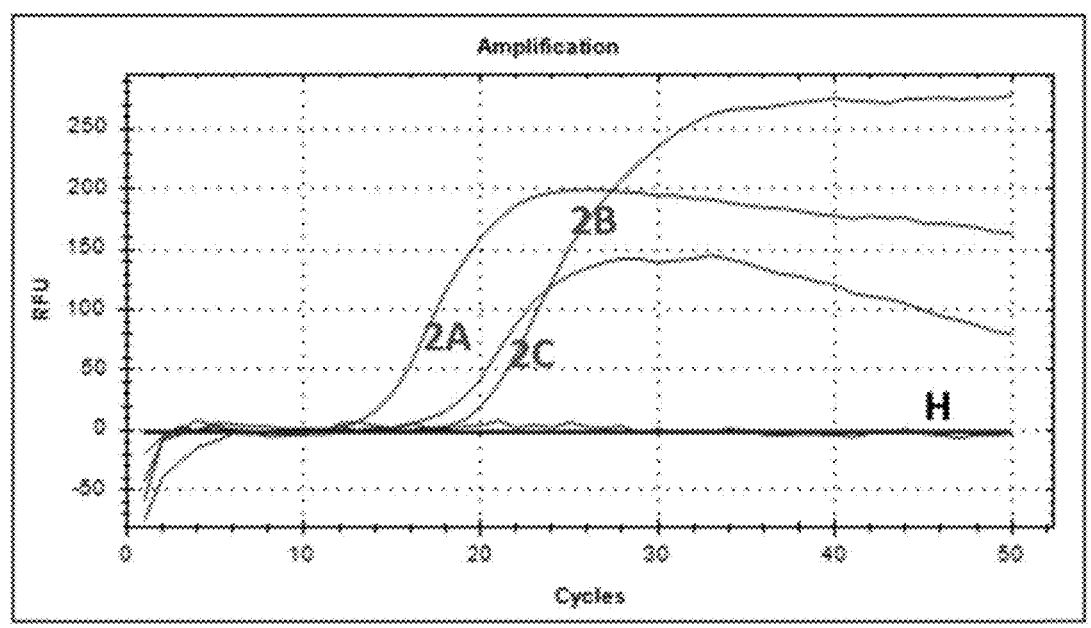
FIG. 2 illustrates the kinetic PCR growth curves of embodiment 1.

FIG. 2 shows the kinetic PCR growth curve for the given pair of primers and probe. When the growth curves of CPV2a, CPV2b, and CPV2c exceed the threshold, an unambiguous and specific signal is initially detectable. In other words, if the sample contains a VP2 sequence, a climbing curve will show in the kinetic PCR growth curve. In the meantime, no signal is detectable of healthy sample because the primer and probe are not specific to the sequence of the healthy sample.

Embodiment 2 Discriminating Wild Type from Vaccine Type by Using SNP 36 by Taqman Probe A. Specificity and Sensitivity Test In order to verify the specificity and the sensitivity for discriminating wild type from vaccine type by using SNP 36, sequences with known copy number are needed to perform the test. The sequences are prepared by the following steps: 1. Clone the wild type and vaccine type of SNP 36 corresponding region into a designated vector respectively. 2. Transform these two factor into *E. coli*. 3. Extract the plasmid DNA. 4. Clarify the sequences are correct with PCR or sequencing.

Four serial single dilutions of the wild type of the SNP 36 of VP2 (hereinafter wild type samples) are prepared with copy number of $10^4$, $10^3$, $10^2$, $10^1$, and three serial single dilutions of the vaccine type of the SNP 36 of VP2 (hereinafter vaccine type samples) are prepared with copy number $10^8$, $10^7$, $10^6$ Primers having SEQ ID NO: 8 for the forward primer and SEQ ID NO: 11 for the reverse primer, and probes having SEQ ID NO: 13 were used to amplify the above-mentioned wild type samples and vaccine type samples. The primer and probe sequences are shown in Table 4.

The forward primers can be replaced to SEQ ID No: 9 or 10, the reverse primers can be replaced to SEQ ID No: 12 or 13, and the probes can be replaced to SEQ ID No: 15. The amplification conditions are identical with the embodiment 1.

TABLE 4

Primer Sequence

Primers used in the examples

| Sequence ID | Function | Sequence 5'-3' |
|---|---|---|
| SEQ ID No: 8 | Forward primer of SNP 36 | ATGAGTGATGGAGCAGTTCA ACCA |
| SEQ ID No: 11 | Reverse primer of SNP 36 | GTACCCGTAGAAATCCCCAC ACCCCAGAAC |
| SEQ ID No: 13 | probe | CAGCAGGCTGACCACC |

TABLE 5

Conditions of the Amplification of SNP 36

|  | Wild type samples | | | | Vaccine type samples | | | NTC |
|---|---|---|---|---|---|---|---|---|
|  | Sample no. | | | | | | | |
|  | 1 | 2 | 3 | 4 | 5 | 6 | 7 | NTC |
|  | Copy no | | | | | | | |
|  | $10^4$ | $10^3$ | $10^2$ | $10^2$ | $10^8$ | $10^7$ | $10^6$ | 0 |
| DNA template |  |  |  | 1 μl |  |  |  |  |
| Primer (F) |  |  |  | 0.5 μM |  |  |  |  |
| Primer (R) |  |  |  | 0.5 μM |  |  |  |  |
| Probe |  |  |  | 0.2 μM |  |  |  |  |
| dNTP |  |  |  | 0.25 mM |  |  |  |  |
| Polymerase |  |  |  | 5 unit |  |  |  |  |
| Total Volume |  |  |  | 20 μl |  |  |  |  |

Figure 3:
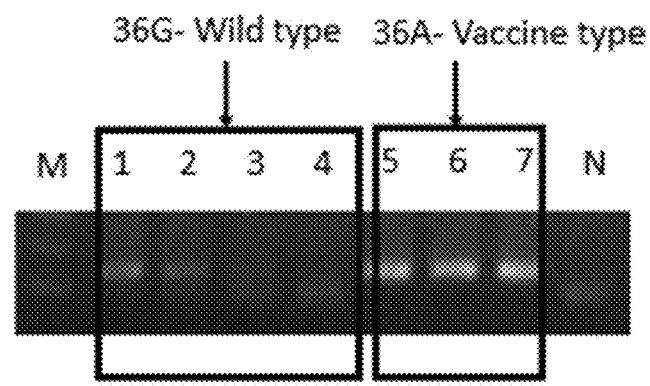
FIG. 3 illustrates the amplification products derived from the embodiment 2 by means of agarose gel electrophoresis. No. 1-4 are wild type samples, and No. 5-7 are vaccine type samples. NTC represents the negative control.

FIG. 3 shows the PCR products of the corresponding region, that is SNP 36 of VP2, by means of agarose gel. The "NTC" represents negative control, and the "M" represents marker. It demonstrates that the PCR reactions with the given primer do exhibit none or less cross reactivity or amplification of unspecific sequences on both wild type samples and vaccine type samples.

Figure 4:
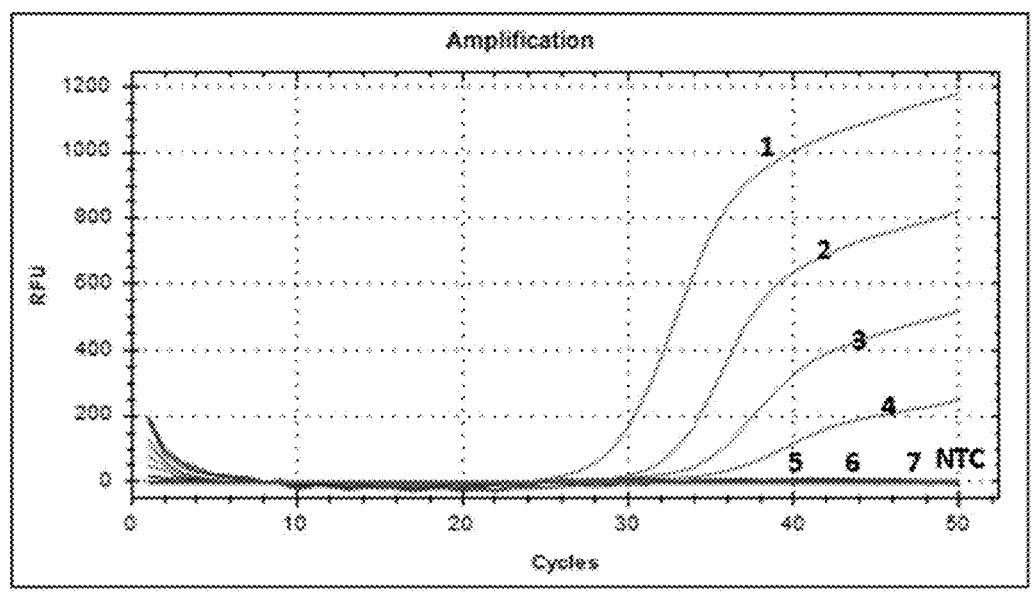
FIG. 4 illustrates the kinetic PCR growth curves of embodiment 2. No. 1-4 are wild type samples, and No. 5-7 are vaccine type samples. NTC represents the negative control.

FIG. 4 shows the kinetic PCR growth curve for the given pair of primers and probe. The probe given in this embodiment is specific to wild type of SNP 36. As above-mentioned, the probe is complementary to "G" since the nucleotide is G for wild type. Therefore, when the growth curve of sample no. 1-4 cross the threshold, unambiguous and specific signal are initially detectable. In the meantime, no signals are detectable of sample 5-7 because that the probe is not specific to "A" where the nucleotide is A for vaccine of SNP 36.

The LOD of this embodiment could reach $10^1$ copy on discriminating wild type from vaccine type. Furthermore, the specificity is relatively high because the discrimination window could reach $10^8$ copy.

B. Authentic Specimen Test

Four authentic specimens and two vaccine bulks (Duramune and Vanguard) are used in this embodiment. The virus DNA of four authentic specimens are also isolated by using an AXYGEN® AxyPrep Body Fluid Viral DNA/RNA. The reason vaccine bulks used in this and the following embodiments is to simulate the sequence type of a vaccinated dog.

Primers sequences, probe sequence, and the amplification conditions are identical to the specificity and sensitivity test. The vaccine bulks are used to carry out the amplification without dilution.

TABLE 6

Conditions of the Amplification of SNP 36 for authentic specimens

|  | authentic specimen Sample no. | | | | | | Vaccine bulks |
|---|---|---|---|---|---|---|---|
|  | 1 | 2 | 3 | 4 | 5 | 6 | NTC |
| DNA template | | | | 1 µl | | | |
| Primer (F) | | | | 0.5 µM | | | |
| Primer (R) | | | | 0.5 µM | | | |
| Probe | | | | 0.2 µM | | | |
| dNTP | | | | 0.25 mM | | | |
| Polymerase | | | | 5 unit | | | |
| Total Volume | | | | 20 µl | | | |

Figure 5:
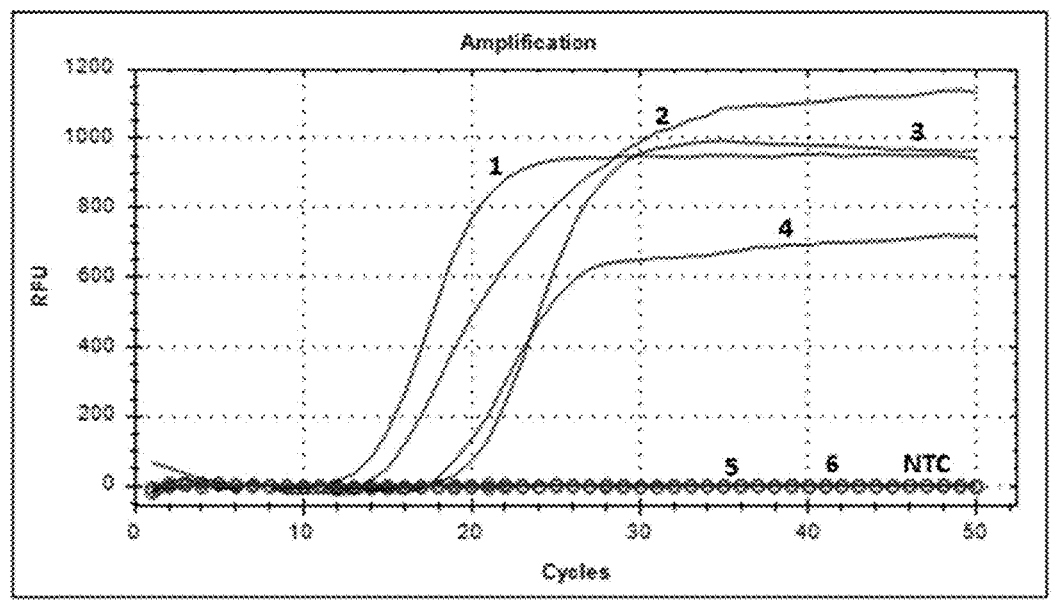
FIG. 5 illustrates the kinetic PCR growth curves of embodiment 2. No. 1-4 are authentic specimens, and No. 5-6 are from vaccine bulks. NTC represents the negative control.
Figure 6:
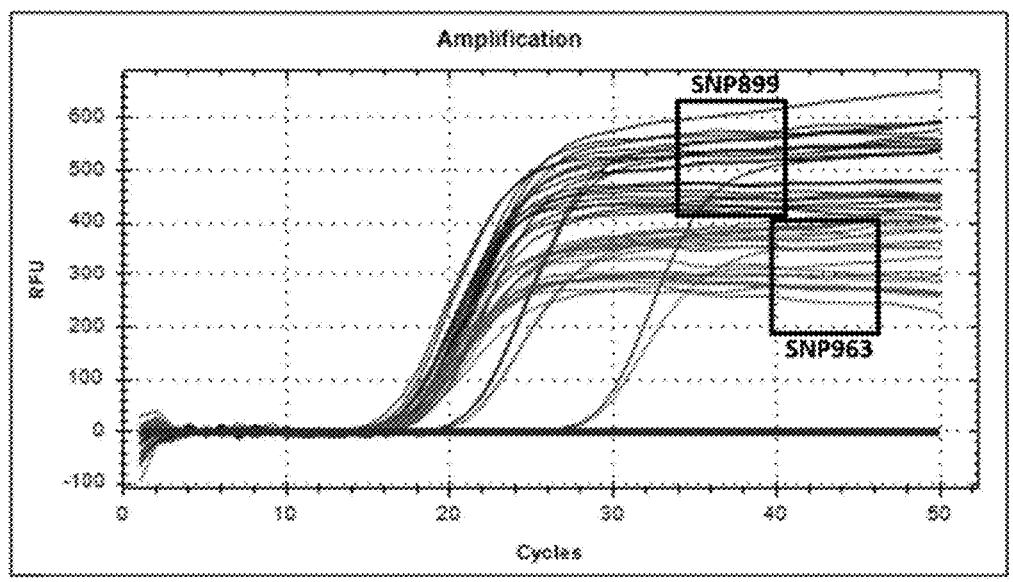
FIG. 6 illustrates the kinetic PCR growth curves of the combination of SNP 899 and SNP963 of embodiment 3. 20 authentic specimens are all positive on both SNP 899 and SNP963.
Figure 7:
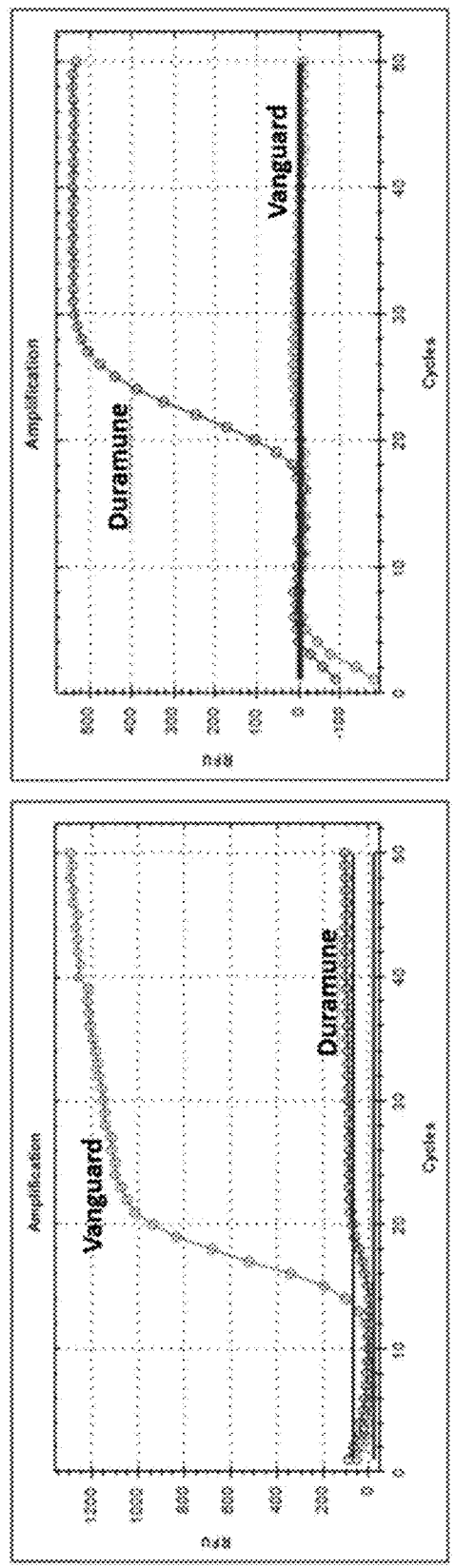
FIG. 7 illustrates the kinetic PCR growth curves of the combination of SNP 899 and SNP963 of embodiment 3. Vanguard bulk is only positive on SNP 963, and Duramune bulk is only positive on SNP 899.

As shown in FIG. 5, four authentic specimens are detectable when their growth curve exceed the threshold. Therefore, these four authentic specimens are wild type since they contain a VP2 sequence. On the other hand, two vaccine bulks are not detectable even if their titer is high.

Embodiment 3 Discriminating Wild Type from Vaccine Type by Using SNP 899 and SNP 963 by Taqman Probe 20 authentic specimens infected by CPV 2a, 2b, and 2c respectively and two distinct vaccine bulks (Duramune and Vanguard) are used in this embodiment. The virus DNA of 20 authentic specimens are also isolated by using an AXYGEN® AxyPrep Body Fluid Viral DNA/RNA.

Primers having SEQ ID NO: 17 which comprises 30 contiguous nucleotides selected from SEQ ID: 16 for the forward primer and SEQ ID NO: 22 for the reverse primer, and probe having SEQ ID NO: 24 for SNP 899 and SEQ ID: 29 for SNP 963 were used to amplify the above-mentioned wild type samples and vaccine type samples. The primer and probe sequences are shown in Table 7. The amplification conditions are as shown is Table 8. The vaccine bulks are used to carry out the amplification without dilution.

The forward primer can be replaced to SEQ ID No: 18, 19, 20, or 21, the reverse primers can be replaced to SEQ ID No: 23, the probe for SNP 899 can be replaced to SEQ ID No: 25, 26, 27, or 28, and the probe for SNP 963 can be replaced to SEQ ID No: 30, 31, 32, or 33. The amplification conditions are identical with the embodiment 1.

TABLE 7

| Primer and Probe Sequence | | |
|---|---|---|
| Primers used in the examples | | |
| Sequence ID | Function | Sequence 5'-3' |
| SEQ ID No: 17 | Forward primer | CAAACAAATAGAGCATTGGG CTTACCACCA |
| SEQ ID No: 22 | Reverse primer | GCACTATAACCAACCTCAGC TGGTCTCATA |
| SEQ ID No: 24 | Probe for SNP 899 | CTGAAGGAGGTACTAACTTT |
| SEQ ID No: 29 | Probe for SNP 963 | TCAAATGGGAAATACAAACT ATA |

TABLE 8

| Conditions of the Amplification of SNP 899 and SNP 963 | | | |
|---|---|---|---|
| | authentic specimen | Vaccine bulks | |
| | Sample no. | | |
| | 1-20 | 21 | 22 |
| DNA template | 1 μl | | |
| Primer (F) | 0.5 μM | | |
| Primer (R) | 0.5 μM | | |
| SNP899 probe | 0.2 μM | | |
| SNP963 probe | 0.2 μM | | |
| dNTP | 0.25 mM | | |
| Polymerase | 5 unit | | |
| Total Volume | 20 μl | | |

As shown in FIG. 6, both SNP 899 and SNP963 are positive on 20 authentic specimens, which means these specimens are truly infected. In contrast with FIG. 6, FIG. 7 shows that there is only one fluorescent signal would be detected if the sample was vaccinated. On the left side of FIG. 7, it shows that the SNP 963 is detectable and the SNP 899 is not detectable because the nucleotide is "T" on SNP 963 which is identical to the wild type, and the nucleotide is "C" which is not identical to the wild type. On the other hand, on the right side of FIG. 7, it shows that the SNP 899 is detectable and the SNP 963 is not detectable because the nucleotide is "G" on SNP 899 which is identical to the wild type, and the nucleotide is "A" on SNP 963, which is not identical to the wild type.

Therefore, if two distinct fluorescent signals are both detectable, it is indicative to the wild type. And if only one signal is detectable, it is indicative to the vaccine type.

Embodiment 4 CPV 2a, 2b, and 2c Detection by Immunochromatographic Assay

One CPV2a infected sample, one CPV2b infected sample, one CPV2c infected sample, and one healthy sample are used in embodiment 4. The DNA was isolated by using an AXYGEN® AxyPrep Body Fluid Viral DNA/RNA. Primers having SEQ ID NO: 34 and SEQ ID NO: 3 were used to amplify a VP2 2a, 2b, and 2c sequence. The primer and probe sequences are shown in Table 2. The probe can also be replaced to SEQ ID No: 5 or SEQ ID No: 6. The labeling of primers and probe used in this embodiment is different from embodiment 1. The 5'-terminal of forward primer carries a DIG, and the 3'-terminal of the probe carries a FITC. The colored particle is colloidal gold.

TABLE 9

| Primer Sequence | | |
|---|---|---|
| Primers used in the examples | | |
| Sequence ID | Function | Sequence 5'-3' |
| SEQ ID No: 34 | Forward primer of VP2 | CTACCACAACAGGAGAAACA CCTGAGAG |
| SEQ ID No: 3 | Reverse primer of VP2 | CCTCCAATTGGATCTGTTGGT AGCAATAC |
| SEQ ID No: 4 | probe | GATTCAAAATATTAAC |

The amplification reaction is carried out which was measured and monitored in real-time on a BioRad CFX Connect Real-time System (BioRad Laboratories, Inc.). Each reaction mixture volume was 20 µl, and was amplified under the following conditions:

TABLE 10

Conditions of the Amplification of the reference samples

|  | 2a | 2b | 2c | Healthy |
|---|---|---|---|---|
| DNA template |  |  | 1 µl |  |
| Primer (F)-DIG |  |  | 0.3 µM |  |
| Primer (R) |  |  | 1 µM |  |
| Probe-FITC |  |  | 0.05 µM |  |
| dNTP |  |  | 0.25 mM |  |
| Polymerase |  |  | 5 unit |  |
| Total Volume |  |  | 20 µl |  |

The reaction mixtures were firstly incubated for 1 minutes at 95° C. The actual amplification reaction was carried out for 50 cycles according to the following scheme:

95° C. 1 sec.→65° C. 1 sec.

Figure 8:
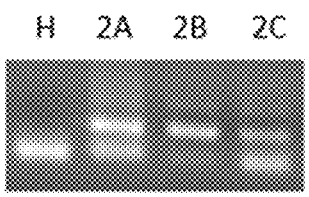
FIG. 8 illustrates the amplification products derived from the embodiment 4 by means of agarose gel electrophoresis.

FIG. 8 shows the PCR products of the corresponding region, that is VP2, by means of agarose gel. The "H" represents healthy sample. It demonstrates that the PCR reactions with the given primer do exhibit none or less cross reactivity or amplification of unspecific sequences on both wild type samples and vaccine type samples.

Figure 9:
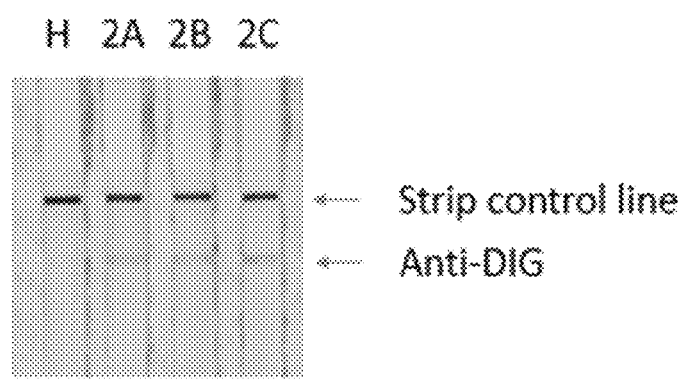
FIG. 9 illustrates the lateral flow of embodiment 4.
Figure 10:
FIG. 10 illustrates the amplification products derived from the embodiment 5 by means of agarose gel electrophoresis.
Figure 11:
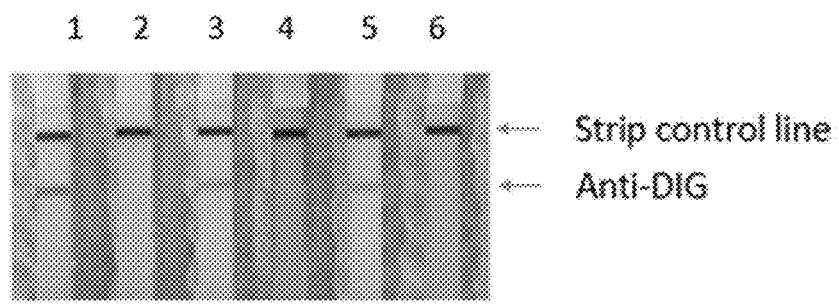
FIG. 11 illustrates the lateral flow of embodiment 5.

FIG. 9 shows the lateral flow for the given pair of primers and probe. When the DIG of CPV2a, CPV2b, and CPV2c meets the anti-DIG and colloidal gold, an unambiguous and specific colored particle is initially visible. In other words, if the sample contains a VP2 sequence, a colored line can be visible on the strip. In the meantime, the colored line of healthy sample is not visible because the primer and probe are not specific to the sequence of the healthy sample.

Embodiment 5 Discriminating Wild Type from Vaccine Type by Using SNP 36 by Immunochromatographic Assay Three wild type specimens and three vaccine bulks are used in this embodiment. The virus DNA of three authentic specimens are also isolated by using an AXYGEN® AxyPrep Body Fluid Viral DNA/RNA. The reason vaccine bulks used in this and the following embodiments is to simulate the sequence type of a vaccinated dog. The labeling of primers and probe used in this embodiment is different from embodiment 2. The 5'-terminal of forward primer carries a DIG, and the 3'-terminal of the probe carries a FITC. The colored particle is colloidal gold. Primers sequences, probe sequence, and the amplification conditions are as below listed.

TABLE 11

| Primer Sequence | | |
|---|---|---|
| Primers used in the examples | | |
| Sequence ID | Function | Sequence 5'-3' |
| SEQ ID No: 8 | Forward primer of SNP 36 | ATGAGTGATGGAGCAGTTCA ACCA |
| SEQ ID No: 11 | Reverse primer of SNP 36 | GTACCCGTAGAAATCCCCAC ACCCCCAGAAC |
| SEQ ID No: 13 | probe | CAGCAGGCTGACCACC |

PNA is added to the amplification to increase the specificity. The vaccine bulks are used to carry out the amplification without dilution.

TABLE 12

| Conditions of the Amplification of SNP 36 for authentic specimens | | | | | | |
|---|---|---|---|---|---|---|
| | authentic specimen | | | Vaccine bulks | | |
| | Sample no. | | | | | |
| | 1 | 3 | 5 | 2 | 4 | 6 |
| DNA template | | | 1 μl | | | |
| Primer (F)-DIG | | | 0.3 μM | | | |
| Primer (R) | | | 1 μM | | | |
| PNA | | | 0.15 μM | | | |
| Probe-FITC | | | 0.05 μM | | | |
| dNTP | | | 0.25 mM | | | |
| Polymerase | | | 5 unit | | | |
| Total Volume | | | 20 μl | | | |

FIG. 10 shows the PCR products of the corresponding region, that is SNP 36 of VP2, by means of agarose gel. Sample 1, 3, 5 are authentic specimens, and sample 2, 4, 6 are from vaccine bulks. It demonstrates that the PCR reactions with the given primer do exhibit none or less cross reactivity or amplification of unspecific sequences on both wild type samples and vaccine type samples.

FIG. 11 shows the lateral flow for the given pair of primers and probe. As above-mentioned, the primers and probe are specific to wild type of SNP 36. Thus, when the DIG of sample 1, 3, 5 meets the anti-DIG and colloidal gold, an unambiguous and specific colored particle is initially visible. In other words, if the sample contains a SNP 36 wild type sequence, a colored line can be visible on the strip. In the meantime, the colored line of vaccine bulk, that is sample 2, 4, 6, is not visible because the primers and probe are not specific to the sequence.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of discriminating a subject of wild type from vaccine type in a sample, comprising:
(f) providing a subject;
(g) providing a pair of primers comprising a first and a second primer wherein the first primer consists of at least contiguous 12 nucleotides of a nucleic acid sequence selected from the nucleic acid sequence SEQ ID NO:16, and wherein the second primer consists of at least contiguous 12 nucleotides selected from the complementary nucleic acid sequences SEQ ID NO: 22 or 23;
(h) amplifying the subject with a template-dependent polymerase;
(i) annealing both P1 and a P2 probes to the subject to form a hybridized product during step (c) wherein the P1 probe is specific to SNP 899 of the VP2 gene of CPV 2a, 2b, or 2c and the P2 probe is specific to SNP 963 of the VP2 gene of CPV 2a, 2b, or 2c, wherein the P1 is selected from a group consisting of SEQ ID NO: 24 to 27, and the P2 is selected from a group consisting of SEQ ID NO:29 to 33; and
(j) detecting two distinct fluorescent signals generating from the hybridized product to indicate the presence of the vaccine type.

2. The method according to claim 1, wherein the first primer is selected from the group consisting of SEQ ID NO: 17 to 21.

3. The method according to claim 2, wherein both the 5'-terminal of the P1 and P2 carry fluorescent reporters which are selected distinct from the group comprising FAM, HEX, VIC, CY5, or TET, and both the 3'-terminal of the probes carry quenchers which are selected from a group comprising TMARA, MGB, or BHQ, and wherein the fluorescent reporters of P1 probe and P2 probe are distinct.

4. The method according to claim 3, wherein the presence of both distinct fluorescent signals is indicative of the wild type, the presence of any one of the distinct fluorescent signals is indicative of the vaccine type.

5. The method according to claim 4, wherein the two distinct fluorescent signals generating from the hybridized product is detected by the quantity of the fragment of the fluorescent reporter which is cleaved from the probe hybridized to the target nucleic acid by an exonuclease hydrolysis of the DNA-dependent polymerase.

6. The method according to claim 5, wherein the primer and/or probe comprise(s) a modified nucleotide or a non-nucleotide compound.

7. The method according to claim 6, wherein the vaccine type is that the sample had once vaccinated with one of the vaccine group including Duramune MX5, Canivac 5, Vanguarad plus 5 L4 CV, Nobivac Puppy DP, Canine 6II-SL, Eurican5, Virbagen DA2Parvo.

* * * * *

SEQUENCE LISTING

<160> NUMBER OF SEQ ID NOS: 34

<210> SEQ ID NO 1

-continued

<211> LENGTH: 1755
<212> TYPE: DNA
<213> ORGANISM: canine parvovirus

<400> SEQUENCE: 1

```
atgagtgatg gagcagttca accagacggt ggtcagcctg ctgtcagaaa tgaaagagct      60
acaggatctg ggaacgggtc tggaggcggg ggtggtggtg gttctggggg tgtggggatt     120
tctacgggta ctttcaataa tcagacggaa tttaaatttt tggaaaacgg atgggtggaa     180
atcacagcaa actcaagcag acttgtacat ttaaatatgc cagaaagtga aaattataga     240
agagtggttg taaataattt ggataaaact gcagttaacg gaaacatggc tttagatgat     300
actcatgcac aaattgtaac accttggtca ttggttgatg caaatgcttg gggagtttgg     360
tttaatccag gagattggca actaattgtt aatactatga gtgagttgca tttagttagt     420
tttgaacaag aaatttttaa tgttgtttta aagactgttt cagaatctgc tactcagcca     480
ccaactaaag tttataataa tgatttaact gcatcattga tggttgcatt agatagtaat     540
aatactatgc catttactcc agcagctatg agatctgaga cattgggttt ttatccatgg     600
aaaccaacca taccaactcc atggagatat tattttcaat gggatagaac attaatacca     660
tctcatactg gaactagtgg cacaccaaca aatatatacc atggtacaga tccagatgat     720
gttcaatttt atactattga aaattctgtg ccagtacact tactaagaac aggtgatgaa     780
tttgctacag gaacattttt ttttgattgt aaaccatgta gactaacaca tacatggcaa     840
acaaatagag cattgggctt accaccattt ctaaattctt tgcctcaagc tgaaggaggt     900
actaactttg gttatatagg agttcaacaa gataaaagac gtggtgtaac tcaaatggga     960
aatacaaact atattactga agctactatt atgagaccag ctgaggttgg ttatagtgca    1020
ccatattatt cttttgaggc gtctacacaa gggccattta aaacacctat tgcagcagga    1080 cggggggggag cgcaaacaga tgaaaatcaa gcagcagatg gtgatccaag atatgcattt    1140
ggtagacaac atggtcaaaa aactaccaca acaggagaaa cacctgagag atttacatat    1200
atagcacatc aagatacagg aagatatcca gaaggagatt ggattcaaaa tattaacttt    1260
aaccttcctg taacagatga taatgtattg ctaccaacag atccaattgg aggtaaaaca    1320
ggaattaact atactaatat atttaatact tatggtcctt taactgcatt aaataatgta    1380
ccaccagttt atccaaatgg tcaaatttgg gataaagaat ttgatactga cttaaaacca    1440
agacttcatg taaatgcacc atttgtttgt caaaataatt gccctggtca attatttgta    1500
aaagttgcgc ctaatttaac aaatgaatat gatcctgatg catctgctaa tatgtcaaga    1560
attgtaactt actcagattt ttggtggaaa ggtaaattag tatttaaagc taaactaaga    1620
gcctctcata cttggaatcc aattcaacaa atgagtatta atgtagataa ccaatttaac    1680
tatgtaccaa gtaatattgg aggtatgaaa attgtctatg aaaaatctca actagcacct    1740
agaaaattat actaa                                                     1755
```

<210> SEQ ID NO 2
<211> LENGTH: 60
<212> TYPE: DNA
<213> ORGANISM: Artificial Sequence
<220> FEATURE:
<223> OTHER INFORMATION: primer

<400> SEQUENCE: 2

```
atagcacatc aagatacagg aagatatcca gaaggagatt ggattcaaaa tattaacttt      60
```

```
<210> SEQ ID NO 3
<211> LENGTH: 29
<212> TYPE: DNA
<213> ORGANISM: Artificial Sequence
<220> FEATURE:
<223> OTHER INFORMATION: Reverse primer of VP2

<400> SEQUENCE: 3
cctccaattg gatctgttgg tagcaatac                              29

<210> SEQ ID NO 4
<211> LENGTH: 16
<212> TYPE: DNA
<213> ORGANISM: Artificial Sequence
<220> FEATURE:
<223> OTHER INFORMATION: probe

<400> SEQUENCE: 4
gattcaaaat attaac                                            16

<210> SEQ ID NO 5
<211> LENGTH: 18
<212> TYPE: DNA
<213> ORGANISM: Artificial Sequence
<220> FEATURE:
<223> OTHER INFORMATION: probe

<400> SEQUENCE: 5
tggattcaaa atattaac                                          18

<210> SEQ ID NO 6
<211> LENGTH: 18
<212> TYPE: DNA
<213> ORGANISM: Artificial Sequence
<220> FEATURE:
<223> OTHER INFORMATION: probe

<400> SEQUENCE: 6
gattcaaaat attaactt                                          18

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
atgagtgatg gagcagttca accagacggt ggtcag                      36

<210> SEQ ID NO 8
<211> LENGTH: 24
<212> TYPE: DNA
<213> ORGANISM: Artificial Sequence
<220> FEATURE:
<223> OTHER INFORMATION: Forward primer of SNP 36

<400> SEQUENCE: 8
atgagtgatg gagcagttca acca                                   24

<210> SEQ ID NO 9
<211> LENGTH: 23
<212> TYPE: DNA
<213> ORGANISM: Artificial Sequence
<220> FEATURE:
<223> OTHER INFORMATION: Forward primer of SNP 36
```

```
<400> SEQUENCE: 9
tgagtgatgg agcagttcaa cca                                        23

<210> SEQ ID NO 10
<211> LENGTH: 27
<212> TYPE: DNA
<213> ORGANISM: Artificial Sequence
<220> FEATURE:
<223> OTHER INFORMATION: Forward primer of SNP 36

<400> SEQUENCE: 10
gagtgatgga gcagttcaac cagacgg                                    27

<210> SEQ ID NO 11
<211> LENGTH: 31
<212> TYPE: DNA
<213> ORGANISM: Artificial Sequence
<220> FEATURE:
<223> OTHER INFORMATION: Reverse primer of SNP 36

<400> SEQUENCE: 11
gtacccgtag aaatccccac acccccagaa c                               31

<210> SEQ ID NO 12
<211> LENGTH: 28
<212> TYPE: DNA
<213> ORGANISM: Artificial Sequence
<220> FEATURE:
<223> OTHER INFORMATION: Reverse primer of SNP 36

<400> SEQUENCE: 12
gaaagtaccc gtagaaatcc ccacaccc                                   28

<210> SEQ ID NO 13
<211> LENGTH: 28
<212> TYPE: DNA
<213> ORGANISM: Artificial Sequence
<220> FEATURE:
<223> OTHER INFORMATION: Reverse primer of SNP 36

<400> SEQUENCE: 13
gtacccgtag aaatccccac accccag                                    28

<210> SEQ ID NO 14
<211> LENGTH: 16
<212> TYPE: DNA
<213> ORGANISM: Artificial Sequence
<220> FEATURE:
<223> OTHER INFORMATION: SNP 36 probe sequence

<400> SEQUENCE: 14
cagcaggctg accacc                                                16

<210> SEQ ID NO 15
<211> LENGTH: 15
<212> TYPE: DNA
<213> ORGANISM: Artificial Sequence
<220> FEATURE:
<223> OTHER INFORMATION: SNP 36 probe sequence

<400> SEQUENCE: 15
cagcaggctg accac                                                 15

<210> SEQ ID NO 16
<211> LENGTH: 961
```

<212> TYPE: DNA
<213> ORGANISM: Artificial Sequence
<220> FEATURE:
<223> OTHER INFORMATION: primer

<400> SEQUENCE: 16

```
atgagtgatg gagcagttca accagacggt ggtcagcctg ctgtcagaaa tgaaagagct        60
acaggatctg ggaacgggtc tggaggcggg ggtggtggtg gttctggggg tgtggggatt       120
tctacgggta ctttcaataa tcagacggaa tttaaatttt tggaaaacgg atgggtggaa       180
atcacagcaa actcaagcag acttgtacat ttaaatatgc cagaaagtga aaattataga       240
agagtggttg taaataattt ggataaaact gcagttaacg aaacatggc tttagatgat        300
actcatgcac aaattgtaac accttggtca ttggttgatg caaatgcttg gggagtttgg       360
tttaatccag gagattggca actaattgtt aatactatga gtgagttgca tttagttagt       420
tttgaacaag aaattttta tgttgttta agactgttt cagaatctgc tactcagcca          480
ccaactaaag tttataataa tgatttaact gcatcattga tggttgcatt agatagtaat       540
aatactatgc catttactcc agcagctatg agatctgaga cattgggttt ttatccatgg       600
aaaccaacca taccaactcc atggagatat tattttcaat gggatagaac attaatacct       660
ctcatactgg aactagtggc acaccaacaa atatatacca tggtacagat ccagatgatg       720
ttcaattta tactattgaa aattctgtgc cagtacactt actaagaaca ggtgatgaat        780
ttgctacagg aacattttt tttgattgta aaccatgtag actaacacat acatggcaaa       840
caaatagagc attgggctta ccaccatttc taaattcttt gcctcaagct gaaggaggta       900
ctaactttgg ttatatagga gttcaacaag ataaagacg tggtgtaact caaatgggaa        960
a                                                                       961
```

<210> SEQ ID NO 17
<211> LENGTH: 30
<212> TYPE: DNA
<213> ORGANISM: Artificial Sequence
<220> FEATURE:
<223> OTHER INFORMATION: Forward primer

<400> SEQUENCE: 17

```
caaacaaata gagcattggg cttaccacca                                          30
```

<210> SEQ ID NO 18
<211> LENGTH: 32
<212> TYPE: DNA
<213> ORGANISM: Artificial Sequence
<220> FEATURE:
<223> OTHER INFORMATION: forward primer

<400> SEQUENCE: 18

```
ggcttaccac catttctaaa ttctttgcct ca                                       32
```

<210> SEQ ID NO 19
<211> LENGTH: 30
<212> TYPE: DNA
<213> ORGANISM: Artificial Sequence
<220> FEATURE:
<223> OTHER INFORMATION: forward primer

<400> SEQUENCE: 19

```
caaacaaata gagcattggg cttaccacca                                          30
```

<210> SEQ ID NO 20

<211> LENGTH: 30
<212> TYPE: DNA
<213> ORGANISM: Artificial Sequence
<220> FEATURE:
<223> OTHER INFORMATION: forward primer

<400> SEQUENCE: 20
tctttgcctc aagctgaagg aggtactaac                                              30

<210> SEQ ID NO 21
<211> LENGTH: 26
<212> TYPE: DNA
<213> ORGANISM: Artificial Sequence
<220> FEATURE:
<223> OTHER INFORMATION: forward primer

<400> SEQUENCE: 21
tctttgcctc aagctgaagg aggtac                                                  26

<210> SEQ ID NO 22
<211> LENGTH: 30
<212> TYPE: DNA
<213> ORGANISM: Artificial Sequence
<220> FEATURE:
<223> OTHER INFORMATION: Reverse primer

<400> SEQUENCE: 22
gcactataac caacctcagc tggtctcata                                              30

<210> SEQ ID NO 23
<211> LENGTH: 30
<212> TYPE: DNA
<213> ORGANISM: Artificial Sequence
<220> FEATURE:
<223> OTHER INFORMATION: Reverse primer

<400> SEQUENCE: 23
acaccacgtc ttttatcttg ttgaactcct                                              30

<210> SEQ ID NO 24
<211> LENGTH: 20
<212> TYPE: DNA
<213> ORGANISM: Artificial Sequence
<220> FEATURE:
<223> OTHER INFORMATION: probe

<400> SEQUENCE: 24
ctgaaggagg tactaacttt                                                         20

<210> SEQ ID NO 25
<211> LENGTH: 20
<212> TYPE: DNA
<213> ORGANISM: Artificial Sequence
<220> FEATURE:
<223> OTHER INFORMATION: probe for SNP 899

<400> SEQUENCE: 25
ctgaaggagg tactaacttt                                                         20

<210> SEQ ID NO 26
<211> LENGTH: 20
<212> TYPE: DNA
<213> ORGANISM: Artificial Sequence
<220> FEATURE:
<223> OTHER INFORMATION: probe for SNP 899

<400> SEQUENCE: 26
tgaaggaggt actaactttg                                          20

<210> SEQ ID NO 27
<211> LENGTH: 21
<212> TYPE: DNA
<213> ORGANISM: Artificial Sequence
<220> FEATURE:
<223> OTHER INFORMATION: probe for SNP 899

<400> SEQUENCE: 27
ctgaaggagg tactaacttt g                                        21

<210> SEQ ID NO 28
<211> LENGTH: 24
<212> TYPE: DNA
<213> ORGANISM: Artificial Sequence
<220> FEATURE:
<223> OTHER INFORMATION: probe for SNP 899

<400> SEQUENCE: 28
agctgaagga ggtactaact ttgg                                     24

<210> SEQ ID NO 29
<211> LENGTH: 23
<212> TYPE: DNA
<213> ORGANISM: Artificial Sequence
<220> FEATURE:
<223> OTHER INFORMATION: Probe for SNP 963

<400> SEQUENCE: 29
tcaaatggga aatacaaact ata                                      23

<210> SEQ ID NO 30
<211> LENGTH: 21
<212> TYPE: DNA
<213> ORGANISM: Artificial Sequence
<220> FEATURE:
<223> OTHER INFORMATION: Probe for SNP 963

<400> SEQUENCE: 30
caaatgggaa atacaaacta t                                        21

<210> SEQ ID NO 31
<211> LENGTH: 23
<212> TYPE: DNA
<213> ORGANISM: Artificial Sequence
<220> FEATURE:
<223> OTHER INFORMATION: Probe for SNP 963

<400> SEQUENCE: 31
tcaaatggga aatacaaact ata                                      23

<210> SEQ ID NO 32
<211> LENGTH: 23
<212> TYPE: DNA
<213> ORGANISM: Artificial Sequence
<220> FEATURE:
<223> OTHER INFORMATION: Probe for SNP 963

<400> SEQUENCE: 32
tcaaatggga aatacaaact ata                                      23

<210> SEQ ID NO 33
<211> LENGTH: 24
<212> TYPE: DNA

```
<213> ORGANISM: Artificial Sequence
<220> FEATURE:
<223> OTHER INFORMATION: Probe for SNP 963

<400> SEQUENCE: 33
actcaaatgg gaaatacaaa ctat                                           24

<210> SEQ ID NO 34
<211> LENGTH: 28
<212> TYPE: DNA
<213> ORGANISM: Artificial Sequence
<220> FEATURE:
<223> OTHER INFORMATION: Probe for SNP 963

<400> SEQUENCE: 34
ctaccacaac aggagaaaca cctgagag                                       28
```